United States Patent
Sutton et al.

(10) Patent No.: US 11,517,285 B2
(45) Date of Patent: Dec. 6, 2022

(54) SUPPORT UNIT FOR A MEDICAL IMAGING ELEMENT

(71) Applicant: KONINKLIJKE PHILIPS N.V., Eindhoven (NL)

(72) Inventors: Jonathan Thomas Sutton, Boston, MA (US); Sean Joseph Kyne, Brookline, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/272,763

(22) PCT Filed: Sep. 4, 2019

(86) PCT No.: PCT/EP2019/073601
§ 371 (c)(1),
(2) Date: Mar. 2, 2021

(87) PCT Pub. No.: WO2020/049054
PCT Pub. Date: Mar. 12, 2020

(65) Prior Publication Data
US 2021/0267572 A1  Sep. 2, 2021

Related U.S. Application Data

(60) Provisional application No. 62/726,761, filed on Sep. 4, 2018.

(30) Foreign Application Priority Data

Oct. 25, 2018  (EP) ..................................... 8202447

(51) Int. Cl.
*A61B 8/00*  (2006.01)
*A61B 5/00*  (2006.01)

(52) U.S. Cl.
CPC .......... *A61B 8/4209* (2013.01); *A61B 5/6834* (2013.01); *A61B 5/0059* (2013.01)

(58) Field of Classification Search
CPC ... A61B 8/4483; A61B 8/4209; A61B 5/6834; A61B 5/0059; A61B 8/4227;
(Continued)

(56) References Cited

U.S. PATENT DOCUMENTS 4,920,966 A * 5/1990 Hon .................... A61B 8/4236
600/459
5,497,771 A    3/1996 Rosenheimer
(Continued)

FOREIGN PATENT DOCUMENTS

CN  206120352 U * 4/2017
EP    2886160 A1 * 6/2015 ............. A61B 8/085
(Continued)

OTHER PUBLICATIONS

International Search Report and Written Opinion for International Application No. PCT/EP2019/073601, filed Sep. 4, 2019, 14 pages.

*Primary Examiner* — Yi-Shan Yang
*Assistant Examiner* — Ashish S Jasani

(57) ABSTRACT

A medical imaging element support unit is for use in fixing a medical imaging element (26) releasably against a region of skin of a subject. The includes a support body (14), having a base for engaging with skin of a subject in use and having a coupling means (22) for releasably coupling the medical imaging element (26) to the support body in use. A pneumatic positioning mechanism facilitates adjustment of a position of the medical imaging element relative to the support body, this being fluidly supplied by an air pump mechanism. The same air pump mechanism facilitates
(Continued)

releasable fixation of the support body (14) to the skin, through creation of a configurable suction force at the skin engagement surface.

14 Claims, 4 Drawing Sheets

(58) Field of Classification Search
CPC ... A61B 8/4281; A61B 8/4245; A61B 8/4263; A61B 8/4272
See application file for complete search history.

(56) References Cited

U.S. PATENT DOCUMENTS

| | | | |
|---|---|---|---|
| 8,409,099 B2* | 4/2013 | Vitek | A61B 8/4483 600/459 |
| 2008/0021317 A1 | 1/2008 | Sumanaweera | |
| 2008/0214953 A1* | 9/2008 | Hashimshony | A61B 5/6834 600/562 |
| 2009/0005690 A1* | 1/2009 | Irland | A61B 8/4281 600/472 |
| 2010/0168577 A1 | 7/2010 | Vezina | |
| 2010/0191277 A1* | 7/2010 | McEwen | A61B 17/1355 606/202 |
| 2014/0235962 A1* | 8/2014 | Yu | A61N 5/1049 600/424 |
| 2015/0065856 A1* | 3/2015 | Tretbar | A61B 8/4236 600/444 |
| 2015/0126871 A1 | 5/2015 | Yoon et al. | |
| 2017/0105700 A1* | 4/2017 | Bar-Zion | A61B 8/0891 |
| 2017/0224305 A1* | 8/2017 | Ho | A61B 8/15 |
| 2018/0168544 A1* | 6/2018 | Davidsen | A61B 8/4254 |
| 2019/0053784 A1* | 2/2019 | Beri | A61B 8/4218 |

FOREIGN PATENT DOCUMENTS

| | | | |
|---|---|---|---|
| JP | 2008061894 A | 3/2008 | |
| WO | 9627325 A1 | 9/1996 | |
| WO | 2014182075 A1 | 11/2014 | |
| WO | WO-2014182075 A1 * | 11/2014 | ......... A61B 8/4254 |
| WO | 2016201006 A1 | 12/2016 | |
| WO | WO-2018060456 A1 * | 4/2018 | ......... A61B 8/0825 |

* cited by examiner

SUPPORT UNIT FOR A MEDICAL IMAGING ELEMENT

RELATED APPLICATIONS

This application is the U.S. National Phase application under 35 U.S.C. § 371 of International Application No. PCT/EP2019/073601, filed on Sep. 4, 2019, which claims the benefit and priority to both Provisional Application Ser. No. 62/726,761, filed Sep. 4, 2018, and European Application No. 18202447.1, filed Oct. 25, 2018, which are incorporated by reference in their entireties.

FIELD OF THE INVENTION

This invention relates to a support unit for a medical imaging element, in particular for use in holding a medical imaging element in contact with a surface of a body.

BACKGROUND OF THE INVENTION

A number of medical imaging modalities make use of imaging elements, such as imaging probes, most notably ultrasound imaging.

In the case of ultrasound in particular, the number of applications of the technology has grown rapidly. Ultrasound has for example become a useful tool to assist clinicians during cardiac management, due to its non-invasive character, and capacity for real time image acquisition. Full volume images of the heart may be acquired at a rate of tens of times per second, from which critical information about cardiac performance can be extracted.

The expansion in range of uses has led to a shift in the way images are collected. Handheld probes, typically used in imaging suites by trained users, remain the standard mode for capturing image data. Experienced users perform an examination of a patient, producing images of interior structures following a defined imaging protocol. Images may be sent to an experienced clinician, such as a radiologist or cardiologist, for interpretation.

However, in addition, in an emergency room environment, ultrasound may be used to monitor bleeding, diagnose trauma, or examine blood flow in a point-of-care fashion. In intensive care units, ultrasound may be used to perform spot checks on the heart to ensure proper anesthesia administration, or verify a response to surgery.

Further to this, there is increasingly a need for holding a probe against a patient's body for an extended period of time, for long-term monitoring or imaging.

Current options to obtain long duration or episodic examinations on patients are quite limited. One approach is to commission a trained individual to hold a probe in place for a long duration, or for instance whenever a spot-check is needed. However, such an approach is resource intensive, consuming valuable personnel, and increasing cost.

There exist a small number of fixation devices for fixing probes to the body for an extended period. These existing approaches are each based on use of large straps for extending around parts of the body, e.g. the circumference of the chest, leg, or head. While this facilitates secure fixation of the probe on the surface of the body, it also requires a large surface area coverage over the body which can be inconvenient or even infeasible for certain procedures or operations. For example, in an emergency or poorly resourced environment, patients may be often be managed hemodynamically, in which instance a non-compact footprint proximal the chest area is not feasible to accommodate. Furthermore, the applied pressure or force of a strap arrangement at the chest may interfere with the process of cardiac stabilization, introducing additional complications.

A strap-based system also largely prevents the possibility of accurate and precise fine adjustment to probe position during an imaging session. Once the probe is articulated to find an optimal view and then locked in place, it is difficult to tweak the surface location and angulation of the probe instantaneously, without releasing and re-securing the strap arrangement. This becomes particularly relevant for instance where a patient moves abruptly, causing the heart to shift slightly in the chest. At this point, fine adjustment of the probe position is necessary.

As an alternative, adhesive-based probe holders are also know. However these too suffer from the deficiency of precluding fine adjustment in position after fixation. Furthermore, the use of ultrasound gel alongside adhesives often prevents robust adhesion to the body surface, particularly when probe position adjustments are required.

Another limitation of adhesive-based approaches aimed at securing a probe to the body is the problem of slipping of the probe after fixation. This can occur simply due to the weight of the probe which, pressing down on compliant skin and sub-cutaneous tissue, causes translation and/or rotation of the probe after the adhesion is activated. This can be a significant problem where there is large fat mass, since here tissue compliance is large, which can therefore lead to deleterious shifting of the probe, making probe fixation very difficult.

A further limitation attendant on both strap-based holders and adhesive approaches is the incapacity to apply normal force to the surface of the body while imaging, while at the same time maintaining stable fixation. During a typical imaging examination, a user may frequently exert force, often of considerable magnitude, on the body being examined. This may in some cases be to reduce an imaging distance between the probe and the target imaged object beneath the skin, and/or may in some cases be to manipulate the probe around or between an intervening structure, such as a rib. When obtaining an apical cardiac view for example, the user may often press a probe between the two most caudal ribs or costal cartilages. This ability is often lost when the probe is fixated using adhesive or straps, degrading image quality.

An improved means of providing fixation of a probe for an extended period is therefore generally required.

Furthermore, in addition to the need for improved fixation of a probe to the body over an extended period, there remains at the same time the need to perform probe angulation, often during the same examination or procedure as there is need for the fixation. Current solutions lack the capacity to easily perform accurate angulation while the probe is fixated, without loss of the stable fixation position.

In addition, increasingly, as applications of ultrasound expand, individuals with less formal training than experienced sonographers are gaining access to the ultrasound modality in their clinical practice. There is hence also a need to facilitate probe position adjustment in a manner accessible to less trained individuals.

In addition, there is also frequently the need during the same operation or procedure to both have the probe fixated for an extended period, and to move the probe manually for manual examination. Manual operation of the probe may be necessary for certain functions, for instance for avoiding shear wave conversion and excessive acoustic power loss, for imaging efficiently off the focal axis in elevation and azimuth, and imaging through compliant, absorptive tissue layers. Current solutions lack the capacity to easily release a probe should manual adjustment or movement of the probe be required.

In conclusion, there remains a need for an improved means of fixing a probe releasably to the body, while at the same time permitting adjustment of the probe position relative to the body.

SUMMARY OF THE INVENTION

The invention is defined by the claims.

According to examples in accordance with an aspect of the invention, there is provided a medical imaging element support unit, comprising:

a support body, a lower exterior face of the body having a skin engaging area, for engaging with skin of a subject in use, and attachment means for receiving and releasably attaching a medical imaging element to the support body in use;

a pneumatic positioning mechanism for adjusting a positioning of a received medical imaging element relative to the support body; and an air pump mechanism;

the air pump mechanism arranged for supplying air to the pneumatic positioning mechanism for adjusting the positioning of the medical imaging element, and the air pump mechanism further controllable in use to create a suction force at the skin engaging area for holding the body against an incident skin surface with which it engages.

The may in some examples for instance be for use with a medical imaging probe.

Thus the solution provided by embodiments of the present invention is to provide a suction source in the form an air pump capable of creating a suction force at a base area of the support body to allow fixing of the support and an attached imaging element or unit (e.g. an imaging probe) to the skin. The use of vacuum-based fixation both eliminates the need for large footprint attachment straps, and also facilitates easy and rapid switching between fixation and non-fixation simply by activating or deactivating the pump, or controlling the level of suction force.

At the same time, it has been realised by the inventors that the same suction mechanism may efficiently be harnessed to simultaneously provide a means of fine position adjustment of the imaging element, without the need for manual manipulation and without an additional source of power or driving force. This can be implemented using a pneumatic positioning mechanism.

Pneumatically driven imaging element positioning allows imaging element position adjustment to be fully or partially automated, allowing scan procedures to be performed by less experienced users, guided by the semi or fully automated control over imaging element positioning. This mechanism may also permit automatic compensation to be implemented against any slippage of imaging element position after fixation.

The benefit of a pneumatic mechanism is that the position adjustment is not directly controlled in dependence upon a level of force or pressure of the supplied air. Rather, position adjustment is in general dependent upon a volume of air contained in each of a plurality of chambers, where the pressure or force of the supplied air used to fill the chambers is not directly relevant to the level of adjustment provided. This means that the same air pump source can be used to independently drive both the controllable suction at the skin contact area (which in general may be dependent on suction force) and the position adjustment, which, due to its pneumatic configuration, is not dependent on the suction force. Hence each can be independently configured using the same air pump source.

In particular, in general, a pneumatic positioning mechanism may comprise one or more pneumatic actuators, each comprising an air chamber, and wherein an actuation displacement of the actuator is dependent on a volume of air in the chamber. For instance, well known examples of pneumatic actuators are pneumatic cylinders in which position of a drive rod received in, and protruding from an end of, the cylinder is adjustable based on a volume of air in the cylinder.

Thus fine adjustment of imaging element position can be implemented while the imaging element remains secured to the body, and without manual manipulation. Optionally, adjustment may be controlled automatically by a controller or processor, permitting fine adjustment to be realised even when operated by a less trained user.

The is for holding a medical imaging element. The medical imaging element may be or comprise an imaging sensor. The medical imaging element may be a medical imaging unit.

A medical imaging element may be in some examples be a medical imaging probe (referred to herein simply as 'probe'). A probe may refer to an imaging probe, in particular a medical imaging probe, such as an ultrasound probe. A probe may in general take any shape. A probe may be a handheld probe, or may be a probe for automatic operation without manual manipulation. In some examples a probe may be elongate, e.g. permitting handheld manipulation through grasping of an elongate body section of the probe. In some examples, a probe may be disk shaped. A probe may in some example consist simply of a transducer arrangement, such as a transducer array or an acoustic stack.

More generally the present invention relates to a support unit for a medical imaging element or device or sensor of any kind. This may include for instance any kind of medical imaging sensor or transmitter, including ultrasound probes and also sensors and transmitters for other imaging modalities such as X-ray or CT. It can have any shape or form and may comprise a single transducer element for instance, or a unit or device having multiple components.

The attachment means may be an adjustable attachment means, permitting adjustment of a position of a received medical imaging element relative to the support body. In some examples, the attachment means may permit swiveling of the received medical imaging element relative to the support body, e.g. may provide a swivel coupling.

In particular examples, the pneumatic actuators may be provided in the form of a bladder arrangement of one or more inflatable bladders, fluidly connected with the air pump mechanism, and the bladders arranged for manipulating a positioning of a received medical imaging element in dependence upon a volume of air in each bladder.

Providing multiple bladders may permit more fine-grained control over position configuration, for instance, permitting more fine control over angulation, by positioning bladders so as to be arranged at different locations about a received medical imaging element.

Control of position adjustment can be achieved using an arrangement of valves, e.g. solenoid valves, to control supply of air into each actuator chamber (e.g. each bladder), and thereby configure a volume of air in each actuator chamber. In this way position configuration is controlled by the valve arrangement, i.e. a position of the medical imaging element is dependent on a configuration of the valves in the valve arrangement. It is not directly related to the force or pressure of supplied air from the air pump. It can therefore be controlled independently to the fixation suction at the base of the support unit.

In particular, each of the one or more actuators may have a respective air inlet supplied by the air pump mechanism, and a respective valve for controlling air supply through the inlet.

This permits independent control of a volume of air in each of the one or more actuator chambers, e.g. each of the bladders.

The pump source can drive the pneumatic positioning mechanism, e.g. the pneumatic actuators, by drawing air from an air inlet from the atmosphere external to the support body and routing it to the pneumatic positioning mechanism. The pump can simultaneously drive the fixation suction at the skin contact area of the unit by drawing air from the skin contact area are routing it to an outlet connected to the atmosphere.

In particular, the air pump mechanism may include a vacuum pump, and a separate air inlet and air outlet fluidly connected to an exterior of the body, and the vacuum pump controllable to drive air from the inlet to the positioning mechanism, and to drive air from the skin engaging area to the outlet.

The vacuum pump thus may be controllable to draw or suck air from the inlet to the positioning mechanism and from the skin engagement area to the outlet. The skin contact area may be connected fluidly upstream of the vacuum pump.

The positioning mechanism may be connected fluidly downstream of the vacuum pump.

The positioning mechanism may be connected fluidly downstream of the suction cavity. In this way air evacuated from the suction cavity serves as at least a partial air source for the pneumatic positioning system.

The air inlet and the suction cavity may together provide an air inflow source for the support unit, in particular for supplying the pneumatic positioning mechanism of the support unit. The air outlet and the pneumatic positioning mechanism may together provide an air outflow for the support unit.

Holding of the medical imaging element can be achieved with different particular configurations.

According to at least one set of embodiments, the support body may have an opening for receiving at least a portion of the medical imaging element in use, the attachment means being arranged to retain the medical imaging element in said opening.

The attachment means may be arranged to hold the medical imaging element in a position adjustable manner within the opening, e.g. in a manner permitting adjustment of orientation. The attachment means may be arranged additionally or alternatively to hold the medical imaging element so as to be swivellable within in the opening. Additionally or alternatively, the attachment means may be arranged to hold the medical imaging element so as to be axially movable in the opening, meaning e.g. up and down in the opening, e.g. up and down relative to the skin contact area.

Where the bladder arrangement is provided, the one or more bladders may be arranged at one or more sides of said opening, and protruding in to the opening. In this way the bladders are arranged for engaging or pressing on (an outer surface of) the medical imaging element received in the opening, permitting manipulation of the medical imaging element position. Where multiple actuators are provided, they may be arranged at different positions at the opening sides, permitting pressing or engaging on the medical imaging element from a range of different directions dependent upon the positions of the bladders. The same concept is applicable also to pneumatic actuators more generally.

In advantageous examples, each of the one or more bladders may be arranged to protrude in to the opening by a distance dependent upon a volume of air in the bladder.

In this way position configuration may be adjusted by adjusting a volume of air in each bladder. By controlling the degree of inflation of each bladder, a force being applied on a received medical imaging element from each of a range of different angles within the opening may be adjusted. In this way e.g. an orientation of the medical imaging element within the opening may be adjusted.

Sides may include any face of the opening, including, where appropriate, an upper or top face.

The support body may according to one or more embodiments include a cavity, the cavity being open across an area of said skin engaging area, and the cavity having an air outlet fluidly connected with the air pump mechanism to permit evacuation of air from the cavity, to thereby create said suction force at the skin engaging area.

The cavity thus forms a suction cavity. The open area to which the cavity opens at the skin engaging area forms a suction area. When the skin engaging area is placed in engagement with skin of a user, the vacuum force created in the cavity creates a suction force at the skin engaging area. This force holds the support unit, and an attached medical imaging element, against the skin.

In examples, the cavity may be formed as a groove in the lower exterior face. The groove may be elongate, i.e. longer (e.g. circumferentially or arcuately longer) than it is wide.

The suction force in use draws skin of a user a small way into the cavity which effectively fixates the body about the location of the suction area. The drawn-in skin acts as a stop against lateral motion of the body over the skin. Hence, use of a cavity not only holds the body against the skin, but also locks the body against lateral motion over the skin.

The outlet from the suction cavity may be located displaced away from the skin engaging area, for instance at an upper region or face of the cavity.

In advantageous examples, the (suction) cavity may be fluidly isolated from the (medical imaging element receiving) opening. This allows the skin fixation control to be kept independent of the medical imaging element position adjustment, i.e. one does not affect the other.

The opening (for receiving the medical imaging element) may be a recess extending into the support body from the skin engaging area, for example a recess in the lower exterior face of the support body, extending into the support body and open at the skin engaging area.

In this case, the opening is closed on one side, e.g. at an upper interior face and open at the other side, forming an open face, e.g. a lower face. The open face forms an open area across the skin engaging area.

The recess may be for fully receiving a medical imaging element in use.

The bladder arrangement may be arranged protruding into said recess in a direction toward the skin engaging face. For instance, the bladder arrangement may be arranged protruding from an upper surface of the recess, the upper surface facing the skin engaging area.

This may allow for axial adjustment of the medical imaging element as well as orientational adjustment, by pressing perpendicularly down on the top of a received medical imaging element. Axial may mean up-and-down, e.g. toward and away from the skin engaging area.

The suction cavity, and e.g. the open area formed at the base of the suction cavity, may be annular, e.g. forming an annular groove in the skin engaging region.

The annular suction cavity may extend around, i.e. surround, the opening for receiving the medical imaging element. By this may be meant that the suction cavity may extend around the region of the skin engaging area occupied by the opening.

According to one or more embodiments, the opening may be in the form of a bore, extending through the support body from one exterior surface to the skin engaging area. This may permit receipt of e.g. an elongate medical imaging element (e.g. an elongate imaging probe), for example through a top of the support body and to the skin engaging area.

A received medical imaging element may in use protrude through a top of the bore. This may permit manual adjustment of a positioning of the medical imaging element in addition to the actuated (mechanized) adjustment provided by the pneumatic positioning mechanism. This provides maximal flexibility with regard adjustment of the medical imaging element position.

According to one or more embodiments, the support unit may further comprise a spacer mechanism comprising a spacer part extending from the lower skin engaging area, and means to permit adjustment of a height of the spacer part from the lower skin engaging area.

Examples in accordance with a further aspect of the invention provide an ultrasound system, comprising a support unit in accordance with any example or embodiment described above or outlined below, or in accordance with any claim of this application, and an ultrasound medical imaging element received in the support unit.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying schematic drawings, in which.

DETAILED DESCRIPTION OF THE EMBODIMENTS

Figure 1:
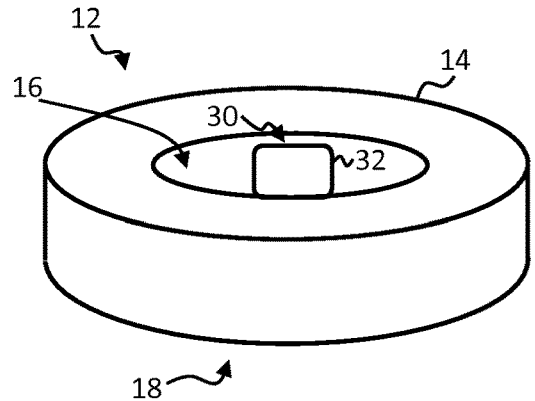
FIG. 1 shows a perspective view of an example support unit in accordance with one or more embodiments.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a support unit for use in fixing a medical imaging element releasably against a region of skin of a subject. The includes a support body, having a base for engaging with skin of a subject in use and having a coupling means for releasably coupling an imaging element to the support body in use. A pneumatic positioning mechanism facilitates adjustment of a position of the imaging element relative to the support body, this being fluidly supplied by an air pump mechanism. The same air pump mechanism facilitates releasable fixation of the support body to the skin, through creation of a configurable suction force at the skin engagement surface.

Embodiments of the present invention relate a support unit for any kind of medical imaging element or unit or sensor or device. This may include an imaging probe. By way of illustration, the following described examples are described with reference to an imaging probe. However this is by way of illustration only, and in each case, the probe may be replaced by any other form of imaging unit or sensor or device without affecting the functioning or technical advantage of the support unit. The described examples are not limited to use of a probe.

Figure 2:
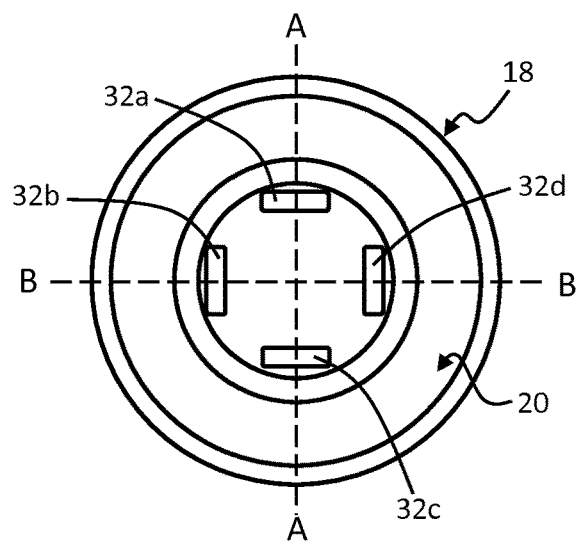
FIG. 2 shows an underside view of the example support unit of FIG. 1.
Figure 3:
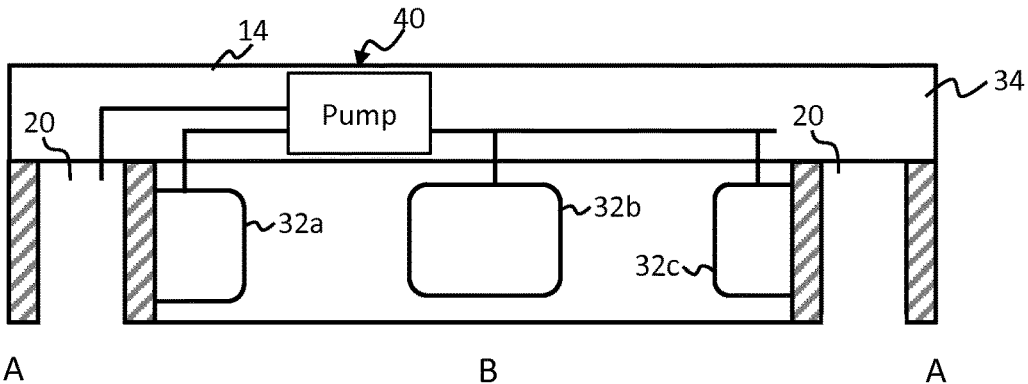
FIG. 3 shows a cross-section through the example support unit of FIGS. 1 and 2.
Figure 4:
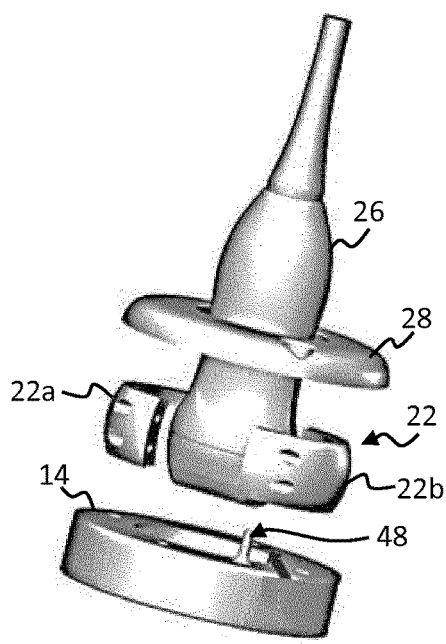
FIGS. 4-6 show perspective views of the example support unit of FIGS. 1-3.
Figure 5:
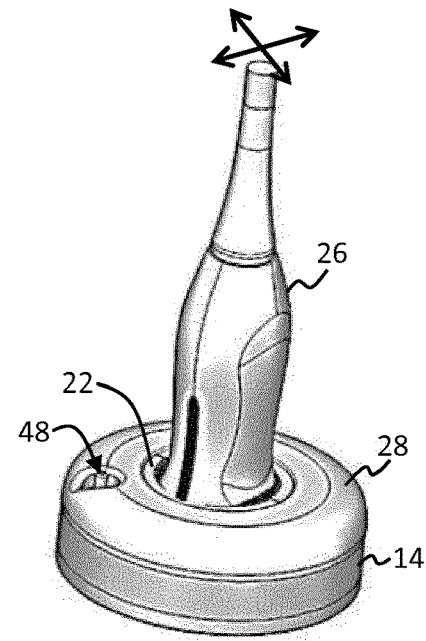
Figure 6:
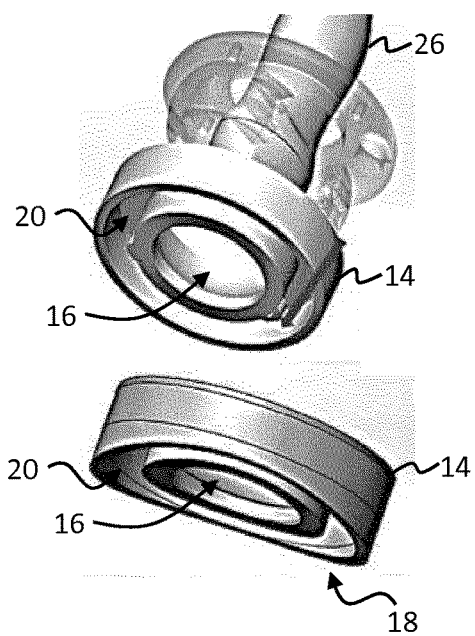

FIGS. 1-6 illustrate various views of an example support unit 12 for a medical imaging element in accordance a first set of embodiments. FIG. 1 shows a perspective view of a support body 14 of the unit. FIG. 2 shows an underside view of the support body. FIG. 3 shows a cross-sectional view through the support body. FIGS. 4-6 show perspective views of the support unit in use, with a probe 26 received in the unit.

The 12 comprises a support body 14. A lower exterior face of the body forms a skin engaging area 18 for engaging with skin of a subject in use. In the present example, the support body has a generally annular shape, delimiting an opening 16 which forms a bore extending through the body from an upper surface of the body to the lower skin engaging area 18. The opening allows receipt of a probe 26 through the support body as shown in FIGS. 4-6. The generally annular shape provides the support body with a torus or disk-like outer shape.

An attachment means 22 is provided for receiving and releasably attaching an imaging probe to the support body in use. The attachment means may take the form of ring grip or clasp element 22 (as shown in FIG. 4) arranged for wrapping around the body of an elongate probe 26 received in the support body to grip the exterior of the probe and hold the probe in place. The attachment element in this example may be formed of two arcuate sections 22a, 22b extending continuously or discontinuously around the probe in use.

Alternatively, the attachment means may be provided simply by one or more components of the pneumatic positioning mechanism 30 (discussed below), e.g. the pneumatic actuators, e.g. inflatable bladders 32, of such a positioning mechanism.

The attachment means in general holds the probe 26 coupled to the support body 14 in use, in position adjustable relationship with the support body, i.e. moveable relative to the support body, e.g. at least orientationally adjustable such as swivellable relative to the support body. The attachment means may be coupled to the support body in a manner permitting tilting, pivoting, rotating and/or swiveling of the attachment means relative to the support body to facilitate the adjustable positioning of a probe held in the attachment means.

For example, in the case of the ring grip element illustrated in FIG. 4-6, an inner radial surface of the bore opening 16 through the support body may dip concavely inwardly, so as to be shaped to receive the attachment element 22 and permit rolling of the attachment about pivoting angles inside the opening. A respective lip or stop protrusion may be provided at an upper and lower edge of this dipped region, to permit retaining of the received attachment means within the bore opening. This may provide a snap-fit coupling between the attachment element and the support body.

Any other attachment means may alternatively be provided, suitable for coupling a probe received in the support body 26 releasably to the support body in position-adjustable relationship to the support body, i.e. moveable relative to the support body.

The attachment element 22 is in this example arranged within the bore opening 16. It is configured to hold a received probe in manner extending through the bore and to the skin contact area 18 to permit contact of the probe with the skin in use. The attachment element is configured so as to be swivellable with respect to the opening, thus permitting swiveling of a received probe within the opening, relative to the support structure.

An attachment element according to any example may be removably coupleable to the support body, e.g. the interior of the opening, for instance adapted to snap fit within the opening.

A pneumatic positioning mechanism 30 is further provided for adjusting a positioning of a received probe 26 relative to the support body 14. In the present example, this is provided in the form of an inflatable bladder arrangement comprising an arrangement of inflatable bladders 32a-32d. These are arranged at a series of positions around sides of the bore opening 16, protruding into the opening, for manipulating the position of the probe through application of pressure. This is shown most clearly in the underside view of the support body 14 of FIG. 2.

In the illustrated example, the bladders are arranged at positions around an annular interior rim of the bore opening. FIG. 3 for example shows a cross-section along line A-A and schematically illustrates the bladders disposed around the interior surface of the opening 16.

The manipulation of the probe by the inflatable bladders 32 is dependent upon a volume of air in an interior air chamber of each bladder, i.e. upon an inflation level of each bladder. In particular, the pressure applied by each bladder on a received probe is dependent upon the volume of air contained therein.

Different configurations for the bladder arrangement 32 are possible. The bladders may in some cases be arranged to apply pressure directly to a received probe. In other cases, they may apply pressure onto an attachment element holding the probe, e.g. the attachment ring illustrated in FIGS. 4-6. In FIG. 3, the bladders are schematically illustrated occupying the whole height of the inner radial surface of the bore opening 16. In this case, the bladders may in use be located radially surrounding a received attachment element 22 within which a probe may be received, and the bladders may apply pressure to the attachment element 22 to manipulate the probe. In other cases, the bladders 32 may occupy only one portion of the height of the radial interior wall of the opening 16, allowing the attachment means to couple to a different portion of the wall, and permitting the bladders to apply pressure to a received probe directly.

The positioning mechanism will be described in greater detail in paragraphs below.

The 12 further comprises an air pump mechanism 40. This may for example be housed in an interior of the probe support body 14 e.g. in an interior cavity or hollow 34 of the support unit. This may for instance be located in an additional region provided above the annular cavity 20 (as illustrated in FIG. 3).

Alternatively, an air pump mechanism may be provided on an upper surface of the probe unit, not housed within a provided cavity. Alternatively again, the pump mechanism may be provided separate to the support body 14 part, e.g. at a base station or unit, and connected with the support body via air pipes.

The air pump mechanism 40 is arranged for supplying air to the pneumatic positioning mechanism 30 for adjusting the positioning of a received probe 26 in use.

The air pump mechanism 30 is further controllable in use to create a suction force at the skin engaging area 18 for controllably holding the support body 14 against an incident skin surface with which it engages. This will be explained further below.

The air pump mechanism may comprise a vacuum pump. The vacuum pump may be powered by a battery, enabling provision of a fully self-contained and wire-free support unit 12 where the battery is provided integrally included in, or coupled to, the support body 14. The power supply may be provided at an exterior of the support body 14, to better electrically isolate the sensing portion of a received probe from the power source, to avoid electrical cross-talk and interference.

The support body 14 in the illustrated example has a shell-like construction, delimiting an annular interior cavity 20, which extends around the central opening 16, which opens onto an annular open area of said skin engaging area 18. In this example, the open area onto which the cavity opens describes a closed annular ring, i.e. it extends continuously around a peripheral region of the skin contact area. The cavity extends around the bore opening through which the probe 26 is received in use. As shown in FIGS. 4 and 5, an air outlet 48 is provided extending from the top of the cavity. This outlet provides fluid connection between the interior of the cavity 20 and the air pump mechanism 40 to permit evacuation of air from the cavity. This creates a vacuum force within the cavity, which thereby creates a suction force at the base of the cavity, where it opens onto the skin engaging area 18.

The suction cavity 20 is preferably narrower than it is circumferentially long, i.e. is preferably circumferentially elongate.

Although the cavity and the open area onto which it opens are annular in this example, this is not essential. It may in other examples be arcuate for instance, or may be a broken or interrupted annular shape. It may be any other shape, and may be formed of a single cavity section or multiple sections, being joined or disconnected. Furthermore, although the cavity is generally circular in the illustrated example, in cases where the cavity is annular, or broken annular, it may be a different shape, such as square, rectangular, triangular, hexagonal or any other annular shape.

The suction cavity 20 is fluidly isolated from the bore opening 16, allowing suction to operate independently of manipulation of the probe.

The air pump mechanism 40 may be operable to provide an adjustable level of suction force between the skin contact area 18 and the skin surface. This may be through providing an adjustable rate of air evacuation from the suction cavity 20, and therefore an adjustable vacuum force in the cavity. The level of suction force may be controllable in accordance with user controls for instance. Alternatively, it may be controlled in accordance with pre-defined settings or a pre-defined control schedule.

The air pump mechanism may include a controller for facilitating provision of adjustable or variable suction force. The suction force may be varied in dependence upon one or more sensor inputs, e.g. pressure sensors (this will be described further below).

As air is evacuated from the suction cavity 20, and the pressure drops between the support body 14 and an incident skin surface with which it is placed in contact, the surface of the skin is drawn slightly into the cavity. This has the effect of increasing the normal force exerted on the skin surface around the points at which the skin is drawn into the cavity. This hence increases the strength of adhesion between the skin and the support body (and hence an attached probe).

In addition, the drawn-in skin effectively acts as a mechanical stop against lateral motion of the support body 14 over the skin surface. The drawn-in skin effectively forms a raised ridge or protrusion which is received within the cavity 20 and about which the sides of the cavity abut. The skin hence effectively forms a stop or block inhibiting lateral movement over the skin. This results in a very sturdy fixation of a received probe 26 in the position that a user desires.

Additionally, the drawing in of skin into the cavity 20 applies a stretching to the skin across the region of contact between the probe and the skin. Since the cavity extends around the probe-receiving opening 16, as skin is drawn into this cavity, the skin across the region circumscribed by this cavity is stretched radially outwardly in a direction toward the cavity. This region of skin is the region covered by the probe-receiving opening 16, and hence a stretching is applied across a region at which a received probe 26 contacts the skin.

This process serves to reduce the surface compliance at the spot of fixation, which helps to overcome the problems of probe slippage which can occur where a probe is fixed onto compliant skin.

Note that the use of interfacing gel, e.g. acoustic coupling gel for ultrasound probe applications, between a received probe 26 surface and the skin surface does not diminish these advantages. Such gel does not hinder sturdy probe fixation, but rather may improve both the smooth translation of the probe over the skin surface, and sealing the interior of the probe adapter to the skin surface for efficient fixation.

Furthermore, the drawing in of skin into the cavity 20 effectively provides a fluid seal around the skin region which makes contact with a probe in use. This provides a further benefit in use of impeding evaporation of interfacing gel applied between the probe surface and the skin surface.

The support body has been tested with use of an ultrasound probe 26. Initial acoustic validation tests have shown no detectable deterioration of image quality over a probe fixation period of 21 hours.

According to advantageous examples, the support unit may be switchable or toggleable between a locked or fixed mode, in which the probe is held locked against the skin, and unlocked or release mode in which the probe is moveable, with the support unit, across the skin. This may be facilitated for example by toggling or switching between a high suction mode of the air pump mechanism and a low suction mode of the air pump mechanism. The strength of suction provided in accordance with each of these modes may be pre-defined, for instance pre-stored in a memory of a controller for the air pump mechanism.

The air pump mechanism 40 may have an air pump with a controllable pumping force for facilitating this functionality. The air pump mechanism may comprise a vacuum pump.

Such examples thus enable toggling between a fixed state and moveable state. The moveable state permits for example manual operation of the probe, for manually conducted scanning, or simply for adjustment of the probe position. In this way, users may for example execute a conventional, e.g. ultrasound, imaging exam, and subsequently toggle to a fixed state by activating the suction feature between the housing and the skin surface. To toggle back to the unlocked state, the suction may be released (or reduced), permitting adjustment of the probe position, before reapplying or increasing the suction to re-fix the probe in the new position.

This hence addresses the problem associated with known strap-based fixation mechanisms, where bi-mode operation (manual scan operation, and fixed-probe scan operation) is very difficult, due to inconvenience of detaching straps. It also addresses of the problem of difficulty of quickly adjusting probe position.

In particularly advantageous examples, the toggling between fixed and release modes may be operable using one hand. For example, easy-access user controls, e.g. one or more control buttons, may be provided. These may be provided for instance on an upper exposed surface 28 of the support body, such that they can be operated e.g. with the little finger of a probe-holding hand. Alternatively, controls might be provided on a received probe. In this case, the support unit 12 may comprise a connection interface for operatively connecting or coupling with a probe to be received in the support unit. This may be a wireless connection interface most optimally.

In most examples, the air pump mechanism 40 includes an electronically powered vacuum pump. However, it is possible alternatively to provide a manually powered vacuum pump, e.g. a hand pumped vacuum bulb, with one way check and release valves. In use, prior to beginning a procedure, a user may pump the bulb to the desired pressure, ensuring that the vacuum is ready to engage at the push of the release valve.

As noted above, the support body 14 includes an attachment means 22 for coupling a probe releasably to the support body.

In general, the attachment means may be arranged such that a probe 26 received in the attachment means occupies a particular defined space, or extends along a minimum defined path relative to the support body. The attachment means should be adapted to hold a received probe in a manner such that the probe in use makes contact with skin to which the support body is placed in contact. Preferably, the attachment means is adapted to hold a probe in manner such that in use one end of the probe is located at the skin contacting area 18.

In different embodiments, the support body 14 may be shaped and dimensioned, and the attachment means 22 may be configured, for receiving and supporting a probe of different particular shapes or sizes.

In the example of FIGS. 1-6, the support unit may be for receiving and supporting a generally elongate probe, as illustrated. In some examples in this case, the support unit comprises an elongate opening in the form of a bore or receiving channel through the body, from one exposed exterior face through to the skin engaging area (i.e. the lower exterior face). This is the example shown in FIGS. 1-6. However, this is not essential. In other examples for instance, the probe-receiving opening 16 may comprise an indent or groove cutting into a side of the support body, the probe arranged to be at least partially received within said groove, e.g. leaning or resting on the grove. In further examples, the opening may be a closed recess formed in the skin-engaging surface of the support body. Such an example is described in greater detail below.

As noted above, the support unit 12 includes a pneumatic positioning mechanism 30 for adjusting a positioning of a received probe 26 relative to the support body 14.

The pneumatic positioning mechanism 30 is in the present example provided in the form of a bladder arrangement, comprising a set of inflatable bladders 32 fluidly connected with the air pump mechanism 40, and the bladders arranged for manipulating a positioning of a received probe 26 in dependence upon a volume of air in each bladder.

The bladders 32 are arranged at one or more sides of said probe-receiving opening 16, and protrude in to the opening. Each bladder 32 is arranged to protrude in to the opening by a distance dependent on a volume of air in the bladder.

The bladders are fluidly supplied by the air pump mechanism 40. The same air pump mechanism drives creation of the suction force at the skin contact area 18, as discussed above.

The air flow configuration of the support unit 12 according to one or more examples will now be described.

Figure 7:
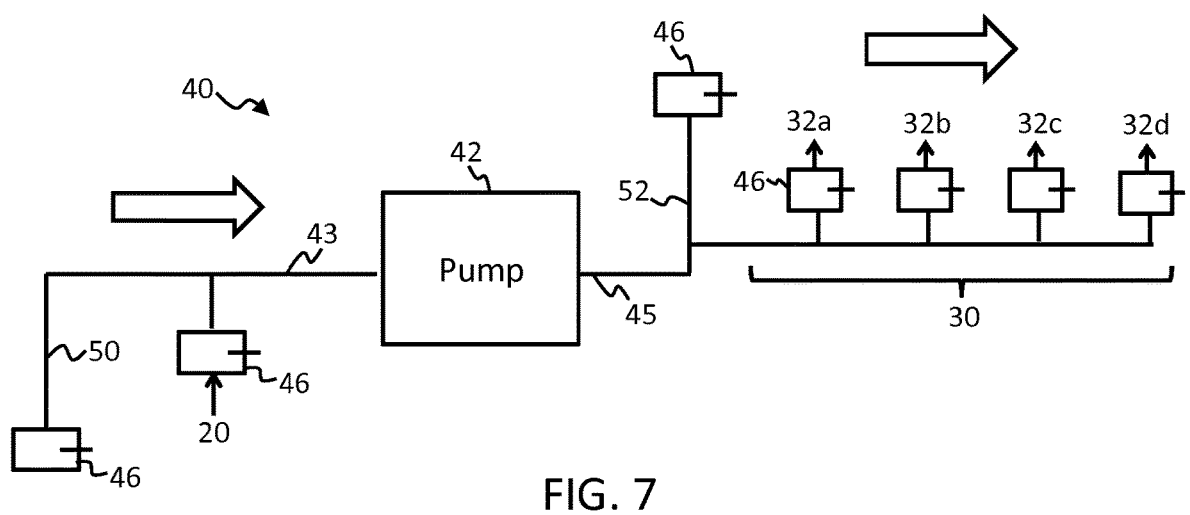
FIG. 7 schematically illustrates an air flow configuration for support units according to one or more embodiments.

FIG. 7 schematically depicts the air flow configuration of the support unit according to one or more examples.

The air pump mechanism 40 comprises a vacuum pump 42. The air pump mechanism 40 further comprises an air inlet 50 and an air outlet 52, the inlet and outlet being separate to one another and both leading to the atmosphere surrounding the exterior of the support unit 12. The inlet and outlet are both fluidly connected with the vacuum pump 42. The inlet and outlet are fluidly connected with the vacuum pump via different branches 43, 45 of an air flow path of the air pump mechanism 40, the inlet being fluidically upstream of the pump (along an in-flow path to the pump) and the outlet being downstream of the pump (along an outflow path of the pump).

The air inlet 50 and air outlet 52 may each be provided with a respective valve being independently controllable between a closed and open state to permit independent control of air flow through the inlet and outlet. The valves may be solenoid valves for example.

The large arrows in FIG. 7 indicate a direction of air flow through the configuration.

The suction cavity 20 is fluidly connected with the vacuum pump 42 via the same fluid path branch 43 to which the inlet 50 is connected, and fluidically upstream of the pump 42. In this way both the suction cavity and the inlet 50 are provided along an air in-flow path leading toward the air pump. The pneumatic positioning mechanism 30 is fluidly connected to the vacuum pump 42 via the same fluid path branch 45 to which the outlet 52 is connected, and fluidically downstream of the vacuum pump 42. In this way, both are provided along an air outflow path leading from the vacuum pump.

The inlet 50 and suction cavity together provide an air inflow source for the support unit 12, in particular for the pneumatic positioning mechanism. The air outlet and the pneumatic positioning mechanism together provide an air outflow for the support unit 12.

As discussed above, the pneumatic positioning mechanism 30 comprises a plurality of inflatable bladders 32a, 32b, 32c, 32d, each provided with a separate air inlet for separately supplying each bladder. The inlet to each bladder 32 is provided with an independently controllable valve 46, permitting independent control of the air flow into each respective bladder. In use, this permits a volume of air in, or inflation level of, each bladder to be independently controlled. The valve may be a solenoid valve.

An outlet may additionally be provided from each bladder 32, leading to an external atmosphere, to permit deflation of the bladders. Each of these outlets may be regulated by an independently controllable valve for example.

The suction cavity 20 is fluidically connected via a controllable valve 46, e.g. a solenoid valve. This is controllable independent of each of the other valves, permitting independent control of suction of air through the cavity.

In use, when the vacuum pump 42 is activated, air is drawn by the vacuum pump from both the atmosphere inlet 50 and the suction cavity 20, along the first fluid path 43 to the pump (provided the valves 46 connecting the cavity and inlet are both open). The in-drawn air is then pumped out from the vacuum pump toward the atmosphere outlet 52 and the inflatable bladders 32. Since the bladders are connected to the pump fluidically upstream of the outlet 52, air supplied from the pump is first provided preferentially to any of the bladders having its respective valve 46 open (in preference over the—further downstream—atmospheric outlet 52). If all of the bladders 32 have closed valves or if there is more air supplied than can be expelled into the open bladders, then the excess air will be expelled through the atmospheric outlet 52.

By controlling the valves 46 of the different bladders 32, an inflation level of each bladder can be independently controlled, thus providing fine control over the positioning of a probe.

The illustrated air flow configuration advantageously permits independent operation of the suction cavity, for driving attachment to skin, and of the pneumatic positioning mechanism, for driving adjustment of the position. The independent valve 46 allows the suction to be completely deactivated if required by simply closing the valve, and the provision of the atmospheric inlet means that such deactivation has no effect on the functioning of the pneumatic positioning mechanism 30.

Furthermore, the level of suction in the suction cavity 20 can also be controlled by simply adjusting a power of the vacuum pump 42. However, such adjustment also has no effect on the functioning of the pneumatic adjustment mechanism, since the flow rate of air is not critical to the operation of the pneumatic bladders. Position control is dependent simply upon air volume in each bladder; the rate at which air is supplied to the bladders from the pump 42 is not important.

Alternatively, a multi-position valve might be provided for regulating outflow from the suction cavity 20. This would permit a suction force within the cavity to be adjusted without altering an overall power level of the pump 42.

Although in the particular example described above, the pneumatic positioning mechanism comprises a bladder arrangement, this is by way of one example only. Different arrangements may be provided in other examples.

More generally for instance, the pneumatic positioning mechanism may comprise one or more pneumatic actuators, each comprising an air chamber, and wherein an actuation displacement of the actuator is dependent on a volume of air in the chamber. The air flow configuration in any such general case may be the same as that described with reference to FIG. 7, with the bladders simply replaced by any other kind of pneumatic actuator.

Figure 8:
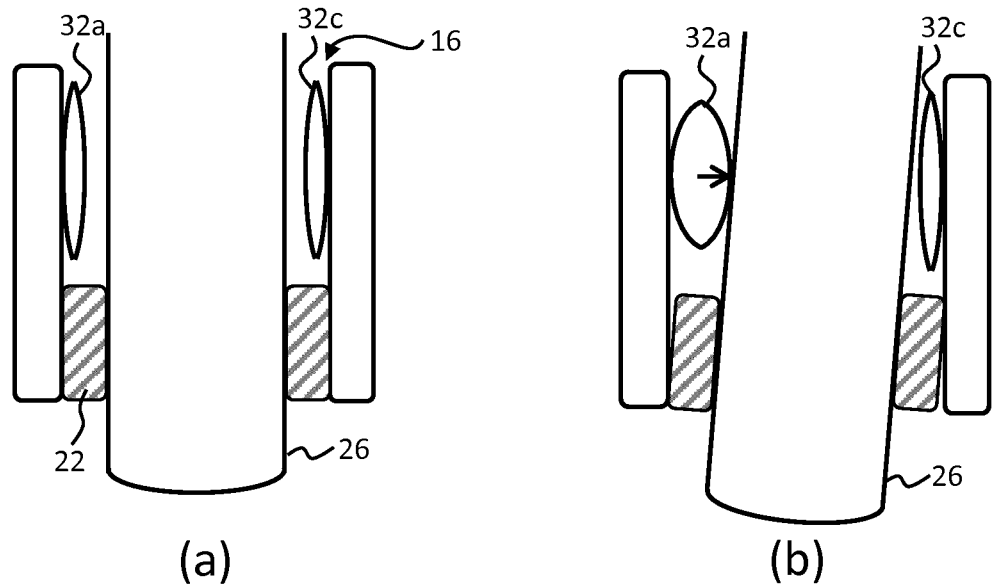
FIG. 8 illustrates operation of an example pneumatic positioning mechanism included in an example support unit according to one or more embodiments.

Operation of the pneumatic positioning mechanism is illustrated schematically in FIG. 8 which shows a cross-sectional view through the example support unit of FIGS. 1-6. The cross-section is along a central plane cutting through the central opening 16, and illustrates a view during use of the device, with a probe 26 received through the opening 16 and held retained in the opening by an attachment means 22.

Two of the inflatable bladders 32a, 32c of the pneumatic positioning mechanism 30 are visible in this view. FIG. 8(a) shows both bladders in an inactive, deflated state. FIG. 8(b) shows one of the bladders 32a in an inflated state. As shown, inflation of the bladder, i.e. increase in the volume of air in the bladder, causes the bladder to protrude by a greater radial distance into the opening 16. This exerts a force upon the side of probe 26 received within the opening, of a magnitude dependent upon a volume of air in the bladder (i.e. upon its level of inflation). In this example, only one bladder is inflated, and hence, a resultant force on the probe 26 is in a direction away from this bladder, toward an opposing side of the opening 16. This causes tilting of the probe 26 away from this bladder and toward the other side of the opening. In this way a position of the probe may be adjusted.

It can be seen that by controlling different combinations of the bladders 32, a positioning of the probe 26 relative to the support body, and hence relative to an incident skin surface can be precisely configured. In particular, an orientation or tilt angle of the probe can be adjusted.

The position adjustment may be manually controlled or automatically controlled, for instance by a controller or processor. Manual control may be via user inputs. The manual control may be mediated by a controller which is configured to convert user input commands into direct control commands for the position adjustment mechanism, in particular the inlet (and possible also outlet) valves 46 for the different bladders. User input commands may be input for instance by a joystick or direction button control, and these commands may be converted by a controller into appropriate valve 46 controls to achieve required inflation levels of each of the bladder 32 to move a received probe 26 to the desired position.

Automatic control may be for instance in accordance with a pre-stored control program or schedule, for instance for performing certain scan procedures or modes. In some examples, the automatic movement of the probe may be guided by scan image data collected concurrently with probe 26 position adjustment. A controller or processor may receive image data and process this data using an algorithm, an output of the algorithm providing further control commands for further moving a probe 26 to continue a scan most effectively. Machine learning algorithms may be employed to train the guidance algorithms in some examples, for instance based on control data associated with expert clinician-operated scans.

Automatic control may additionally or alternatively provide auto-adjustment to counter any slippage or displacement of probe 26 position after vacuum fixation of the probe 26 and support body 14 in a particular position.

As mentioned above, the particular shape and form of the support unit may vary in dependence upon the particular variety of probe with which it is intended to be used. The example of FIGS. 1-6 is shaped for receiving e.g. an elongate probe 26 through the bore opening 16. Such probes are typical for instance of cardiac sector probes.

A support body may however be provided configured for receiving a different kind of probe, e.g. a compact probe, or a patch probe.

The attachment means 22 may be provided specific to the type of probe. For instance, the interior profile of a ring-grip type attachment element may vary depending upon the diameter of the intended probe. FIGS. 1-6 show a support unit having a size appropriate for parasternal cardiac examinations for example. The may be smaller in other examples, for receiving a smaller probe for other imaging applications, such as abdominal or muscoskeletal.

The example of FIGS. 1-6 is a support unit having an annular ring construction, arranged to wrap around the body of an elongate probe, the probe being received through a bore opening 16 extending through the middle of the support body 14

Other configurations are also possible.

Figure 9:
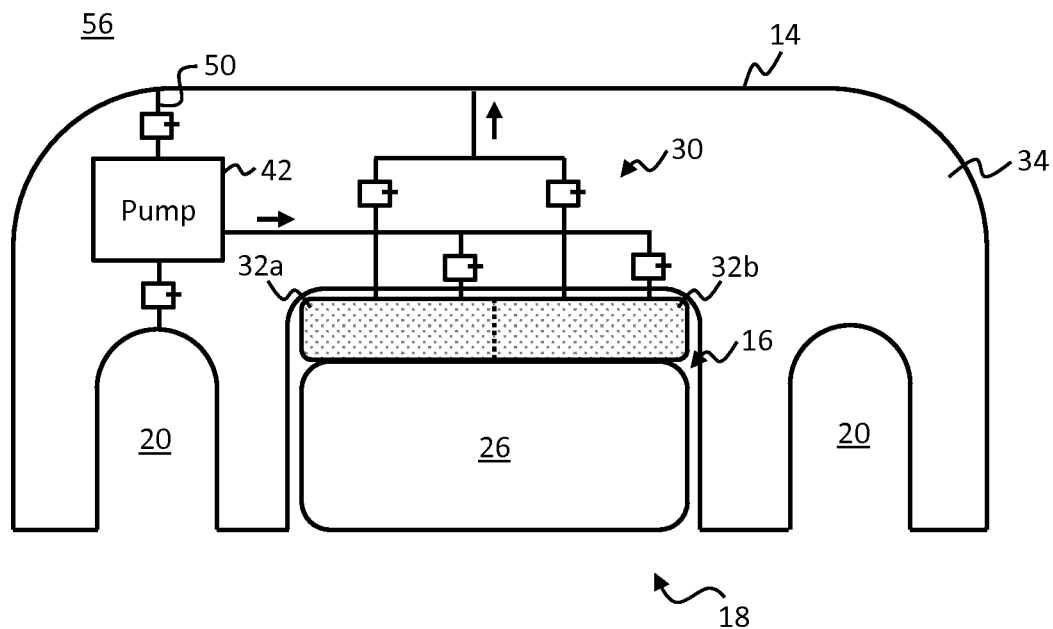
FIG. 9 shows a cross-sectional view of a further example support unit according to one or more examples.

FIG. 9 schematically depicts a cross-sectional view through a further example support unit according to one or more examples.

This example also has a round, generally annular shape, extending around a central opening 16. However, the opening in this example is in the form of a recess formed at the skin engaging surface 18 and extending into the support body 14. The is configured for receiving a compact, squat imaging probe 26, the probe being received into the recess opening 16 via the skin contact area 18. The imaging probe may comprise an acoustic stack.

A pneumatic positioning mechanism 30 is provided in the form of a bladder arrangement comprising a plurality of inflatable bladders (as in the example of FIGS. 1-6). The bladders 32 of the bladder arrangement in the present example are arranged protruding into the recess opening in a direction toward the skin engaging face 18 of the support body 14.

Optionally, the bladder arrangement is arranged protruding from an upper surface of the recess 16, the upper surface facing the skin engaging area 18.

In the illustrated example, the bladder arrangement is provided in the form of a bladder sheet 60, comprising a plurality of bladders 32 formed as individual sealed pockets or chambers in a single continuous article. This bladder sheet is provided disposed above the probe 26 in the recess opening 16. In this way, orientational manipulation of the probe within the recess can be provided.

Only two of the bladders of the bladder sheet are visible in the view shown in FIG. 9. However, in the present example, the bladder sheet comprises four bladders 32. The bladder arrangement may however comprise any number of bladders. The air flow paths to and from each of the visible bladders is shown in FIG. 9. Each bladder has a respective inlet and outlet, flow through each independently controllable with respective valves. The valves may be solenoid valves for instance. The inlets permit inflow of air for inflation of a respective bladder. The outlets permits escape of air for deflation of the bladders.

A vacuum pump 42 is further provided for fluidly supplying the positioning mechanism 30 and for creating a suction force within the suction cavity 20. The vacuum pump is arranged to draw air from both the suction cavity 20 and from the atmosphere 56 surrounding the exterior of the support unit. For this purpose, the pump is fluidly connected to the suction cavity 20 and to an inlet 50 which is fluidly connected to an exterior of the support unit 12.

The pump 42 is arranged to drive the sourced air to the bladders 32 of the positioning mechanism 30. Further downstream from the position mechanism 30 is also a further outlet 52 leading to the exterior of the support body 14, for fluid connection to the atmosphere surrounding the support body 14. This is so that excess air evacuated from suction cavity 20 which is not able to escape into the positioning system can escape to the atmosphere.

The vacuum pump and flow path arrangement, including the various valves, is housed within an interior cavity 34 in an upper region of the support body 14.

As in the example of FIGS. 1-6, a suction cavity 20 is provided in the support body 14 which opens onto an open area at the skin contact area 18 at a base of the support body 14. The cavity is annular, and extends annularly around the recess opening 16.

Figure 10:
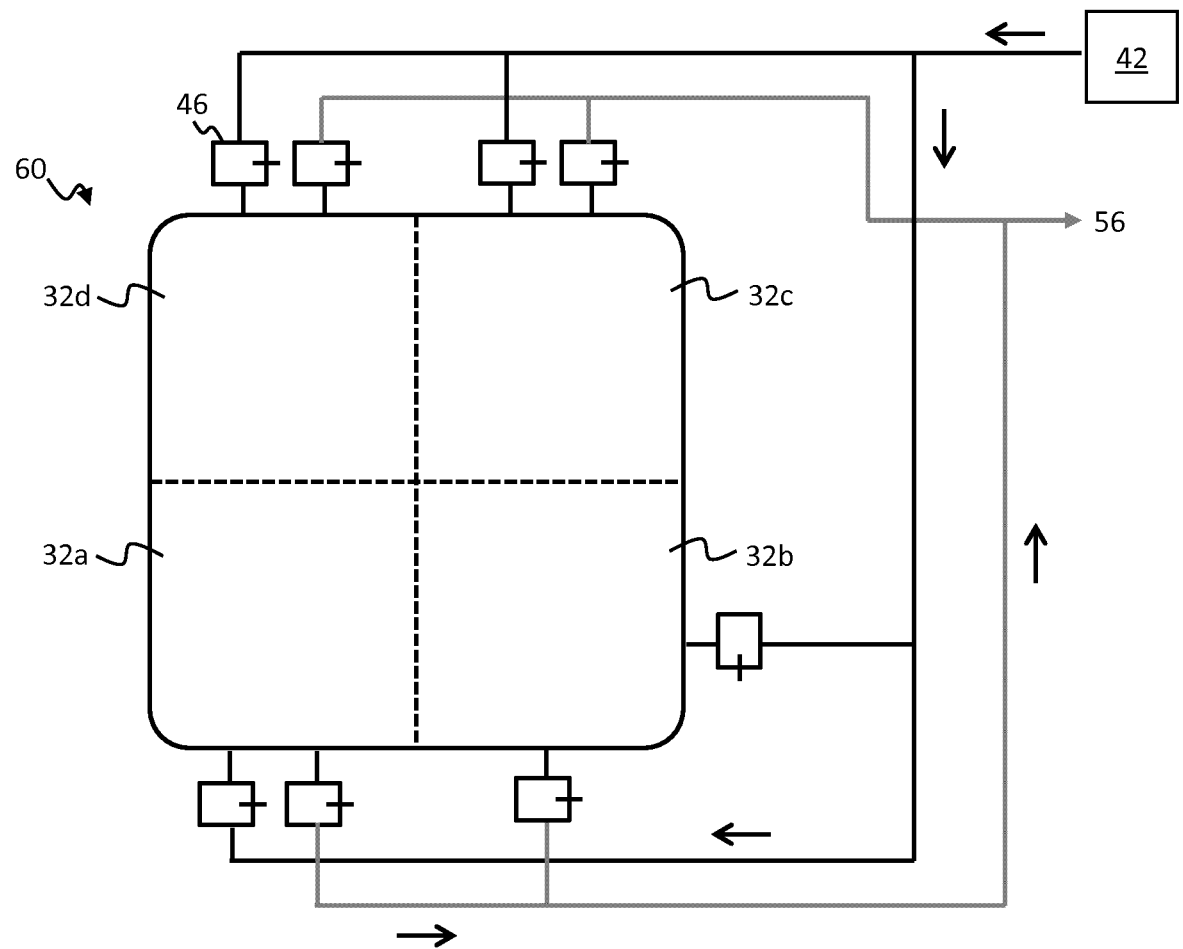
FIG. 10 shows an example pneumatic positioning mechanism as may be included in the example support unit of FIG. 9.

The bladder arrangement comprising bladder sheet 60 is illustrated in more detail in FIG. 10, along with the air flow arrangement. The bladder arrangement comprises four bladders 32a, 32b, 32c, 32d, formed as sealed pockets in an integral sheet article.

Each bladder is fluidly connected with the vacuum pump 42, each via an individually controllable inlet valve 46. Each is also supplied with a respective outlet, for permitting escape of air, to deflate the respective bladder. Each outlet is individually controllable by respective outlet valve. The outlets lead to an atmosphere 56 outside of the support body 14.

The bladder sheet arrangement 60 essentially provides a planar array of inflatable bladders 32 which in use extend over the top of a received probe 26. This arrangement advantageously enables movement of the probe both orientationally (through inflating the set of bladders in uneven configurations) and also axially, i.e. in an up and down direction (through inflating the bladders with equal amounts of air, so as to apply a force in the downward 'z' direction). By inflating different of the bladders with varying amounts of air, the probe can be tilted freely in various directions. By inflating all four of the bladders evenly with varying quantities of air, different axial (up-down) positions of the probe can be achieved.

In accordance with any embodiment of the present invention, one or more pressure or force sensors may be provided for sensing a force between a skin engaging surface 18 of the support body 14 and a surface of skin with which it is engaging. An output of such sensor(s) may for example be used to inform adjustment of a level or force of suction provided at the skin engaging area 18. This may be through adjusting a power or flow rate of the vacuum pump 42 or in some examples through adjusting degree of closure of a multi-position valve outlet 46 of the suction cavity 20.

For example a controller may be provided with a pre-stored or pre-defined set of appropriate levels of suction (e.g. vacuum power levels) for each of a corresponding set of force sensor outputs. When force is low, it is an indication that a strength of adhesion or coupling between the support unit 14 and the skin surface with which it is engaging is low. In this case, suction strength may be increased. In the case that force output is sensed to be high, it may be an indication that a strength of coupling may be uncomfortably high for a patient, and hence suction strength may be reduced.

Additionally or alternatively, a pressure transducer may be provided within the suction cavity 20 to measure air pressure. The level of air pressure in the suction cavity is directly related to a strength of the vacuum force created at the open base of the cavity, and hence of the suction force being created at the base. This may additionally or alternatively be used to guide adjustment of the level of suction, e.g. of the power or flow rate of the vacuum pump 42.

To protect or cushion sensitive skin, and/or assist in probe navigation, according to any embodiment of the present invention, there may be provided in addition to the support body 14, a coupling pad or coupling layer for interfacing between the skin and a probe held in the support body in use. The coupling layer is disposed across a region of skin to which the probe is to be applied, and provides a cushioned surface onto which the probe and support body can be applied.

The coupling pad is formed of an acoustically transparent, compliant material. The coupling pad preferably includes a layer of adhesive across its base for coupling the pad to the skin. The support body 14 then vacuum-couples to this adhered pad instead of directly to the skin surface, thus protecting the skin from the strong forces associated with the suction coupling. In addition, a probe 26 received in the support body also interfaces with the pad. Free translation of the probe over its exposed surface is possible.

Thus, bruising and skin irritation which may result after prolonged use in some individuals can be avoided. Also, for individuals with sensitive skin, direct contact with the skin may not be possible.

In some examples, to provide guidance for less experienced users, the pad may include printed graphics on its exposed surface indicating locations of certain landmarks for specific examination types. For example, pads for cardiac imaging may include graphics indicating locations such as the nipple, intercostal spaces, sternum, and shoulder vectors. Markers for different exam types can be printed in various colors for repeated use of the same pad.

In some examples, one or more sensors may be integrated in the pad, for instance for measuring one or more physiological parameters, or for measuring physical parameters associated with the position of the pad relative to the skin and/or the pressure between the pad and the applied probe. Such sensors may include, but are not limited to, one or more of the following: ECG sensor, PPG sensors (e.g. for measuring respiration), passive ultrasound detectors, strain gauges, gyroscopes and accelerometers.

The one or more sensors may be embedded in the pad or may be provided at one or both of the surfaces of the pad. A controller may further be provided, and the sensors may be communicatively coupled with the controller, e.g. via a wireless communication link.

In any embodiment of the present invention, the support body 14 may further comprise a spacer mechanism comprising a spacer part protruding from the lower skin engaging area 18, and means to permit adjustment of a height of the spacer part from the lower skin engaging area. This spacer, or stand-off, mechanism allows for adjustment of protuberance of a received probe from the support body. The spacer part effectively provides an adjustable foot, allowing extension of the height of the support body 14 base. In this way the extent to which a probe received in the support body protrudes can be adjusted.

This enables variable axial force between a received probe (after fixation of the support body 14) and the body surface, e.g. the chest. Such adjustment is required in certain cases, for example in certain cardiac ultrasound exams such as for apical cardiac views. In general, this feature changes the degree of protuberance of a probe head from the support body.

As the thickness of the spacer decreases, the degree of protuberance of the probe increases, resulting in more axial force of the probe on the surface of skin, and greater suction force required to maintain fixation.

In some examples, the spacer may be provided with a slightly contoured surface, enabling more efficient fixation on curved surfaces, especially when fixated for instance in a horizontal configuration. This may permit easier accommodation of more difficult viewing windows, such as the apical cardiac transthoracic view.

The adjustable spacer mechanism may be implemented in at least two main ways. In a first example, the spacer part may be formed of a stack of detachable spacer pieces. By adding or removing pieces, the height of the spacer can be adjusted. The pieces may be formed of differing thicknesses to permit maximal adjustability of the height. The lowermost pieces may be configured to press or snap fit to a base of the support body 14.

According to an alternative example, the spacer part may be retractably extensible from the base of the support body, for instance in dependence upon rotation of a dial, e.g. a threaded dial. The dial may hand-rotatable by the user to change the degree of protuberance. The spacer part may for instance be retractably received within a cavity in the base, for shortening the spacer, and then retracted out from the cavity again for lengthening of the spacer.

In either example, an exposed surface of the spacer may be coated with a smooth, silicone material for easy sliding over a skin surface, in particular when ultrasound gel is present. A silicone surface also permits creation of a tight seal against the skin when the support body is in fixed mode.

In either example, the spacer may extend annularly around a peripheral region of a base of the support body. The spacer part may hence be annular in construction. The spacer may be other shapes in further examples. Multiple spacers may be provided disposed at various points on the support body base, for instance at different positions around a periphery of the base.

As discussed above, a support unit in accordance with embodiments of the present invention may be provided in various sizes and configurations in order to accommodate probes of different sizes and shapes, for use for different applications.

For example, various embodiments of the support unit may be configured to accommodate conventional handheld elongate probes, or smaller compact form factor probes. Different probe sizes can be accommodated by use of probe-specific attachment elements 22 for attaching the probes to the support body 14 or by changing the overall form factor of the support body 14.

Although certain examples discussed above are described with reference to use of the support unit with an ultrasound imaging probe, this is by way of one example use only. The according to the invention may be advantageously employed for assisting holding of any of a wide range of medical sensors or medical imaging elements or units, employing modalities different from ultrasound.

By way of example, the support unit may be advantageously employed for holding handheld medical sensors or medical imaging elements, i.e. sensors or elements small enough to be held in the hand. However, by appropriately selecting dimensions of the support unit, larger medical imaging elements or medical sensors might also be used with the support unit. As discussed above, the support unit may be used with both elongate shape medical sensors and medical imaging elements or units with different shapes, such as more flattened medical sensors or imaging elements.

By way of one example application, the support body according to embodiments of the invention may be employed for holding an ultrasound unit or element.

By way of another example application, the support body according to embodiments may be employed for holding an optical-based medical sensor or medical imaging element. Such elements are based on directing light into the body. Such elements would in many cases benefit from employment of the support body for controlled application to the body. This would ensure good optical coupling with the body for example.

The support body would be advantageous for example for use in holding a PPG or $SpO_2$ sensor or element. These sensors are typically small, and operate based on directing light (or other electromagnetic energy) through the skin to measure parameters associated with blood flow and cardiac operation (e.g. pulse rate). Such sensors would benefit in many cases from controlled application to the body, to ensure good optical coupling with the skin.

By way of further example, the support body may be advantageously employed for holding photo-acoustic based sensors or imaging elements. These sensors and elements are based on use of the photo-acoustic effect. Here, optical energy (e.g. non-ionizing laser pulses) are directed into tissue. This is absorbed at a molecular or atomic level and converted into heat, leading to temporary thermo-elastic expansion. This leads to ultrasonic emission by the tissue, which can be detected by additionally placed ultrasound transducers. Analysis of the detected emission allows images to be produced. The magnitude of the ultrasonic emission is also by itself indicative of certain physiological parameters. The support body according to embodiments may be advantageously employed for holding the optical emitter against the skin for example, or for holding the transducers against the skin, or both.

The above represent example applications only. The may be advantageously employed for holding a medical sensor or imaging element of any type and any modality. Its advantages in terms of enabling hand-free holding and intelligent position adjustment are not bound by the particular sensing or imaging modality of the element held by the support unit.

Cardiac examinations may in examples be performed using support bodies of varying size and contour to accommodate parasternal, apical, or subcostal views.

By way of example, transcranial examinations might be performed in combination with the coupling pad noted above and for instance using a miniaturized ultrasound probe.

Musco-skeletal and vascular scanning applications may in some examples be implemented using a conventional elongate probe, or a compact probe, for instance attached to the leg or arm by means of a support unit according to one or more embodiments, during or after a surgical procedure or during exercise.

Embodiments of the present invention may be used to guide biopsy procedures, by coupling a probe proximal to a point of entry of the biopsy needle, to guide the biopsy needle into the tissue.

In some examples, means may be provided for mechanically or pneumatically actuating the biopsy needle, for assisted guiding or placement of the needle within the ultrasound image space. This may improve accuracy of needle placement in some examples.

Examples in accordance with a further aspect of the invention provide an ultrasound system, comprising a support unit in accordance with any embodiment or example described above or in accordance with any claim of this application, and an ultrasound probe received in the support unit.

As discussed above, certain embodiments may optionally make use of a controller in some examples.

A controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A medical imaging element support unit, comprising:
   a support body, a lower exterior face of the support body having a skin engaging area, for engaging with skin of a subject in use, and attachment element for receiving and releasably attaching a medical imaging element to the support body in use;
   a pneumatic positioning mechanism for adjusting a positioning of the received medical imaging element relative to the support body; and
   an air pump mechanism;
   the medical imaging element support unit characterized in that:
   the air pump mechanism arranged for supplying air to the pneumatic positioning mechanism for adjusting the positioning of the received medical imaging element, and
   the air pump mechanism further controllable in use to create a suction force within the support body, the suction force proximate to the skin engaging area for holding the support body against an incident skin surface with which it engages.

2. The medical imaging element support unit as claimed in claim 1, wherein the pneumatic positioning mechanism comprises one or more pneumatic actuators, each comprising an air chamber, and wherein an actuation displacement of the one or more pneumatic actuators is dependent on a volume of air in their respective air chambers.

3. The medical imaging element support unit as claimed in claim 2, wherein the one or more pneumatic actuators each comprise an air chamber, wherein the air chamber is provided in the form of a one or more inflatable bladders, fluidly connected with the air pump mechanism, and the one or more inflatable bladders arranged for manipulating the positioning of the received medical imaging element in dependence upon a volume of air in each inflatable bladder.

4. The medical imaging element support unit as claimed in claim 3, wherein the one or more inflatable bladders are arranged at one or more sides of an opening for receiving at least a portion of the medical imaging element, and wherein the one or more inflatable bladders are arranged to be protruding into said opening.

5. The medical imaging element support unit as claimed in claim 4, wherein each of the one or more inflatable bladders is arranged to protrude in to the opening by a distance dependent upon a volume of air in the inflatable bladder.

6. The medical imaging element support unit as claimed in claim 3, wherein an opening for receiving at least a portion of the medical imaging element is a recess extending into the support body from the skin engaging area, and wherein the bladder arrangement is arranged protruding into said recess in a direction toward the skin engaging area, and optionally wherein;
   the bladder arrangement is arranged protruding from an upper surface of the recess, the upper surface facing the skin engaging area.

7. The medical imaging element support unit as claimed in claim 2, wherein each of the one or more actuators has a respective air inlet supplied by the air pump mechanism, and a respective valve for controlling air supply through the air inlet.

8. The medical imaging element support unit as claimed in claim 1, further comprising:
   a separate air inlet and air outlet fluidly connected to an exterior of the support body;
   wherein the air pump mechanism includes a vacuum pump the vacuum pump controllable to drive air from the air inlet to the pneumatic positioning mechanism, and to drive air from a cavity formed by the support body to hold the skin engaging area against the incident skin surface.

9. The medical imaging element support unit as claimed in claim 1, wherein the support body has an opening for receiving at least a portion of the medical imaging element in use, the attachment element being arranged to retain the received medical imaging element in said opening.

10. The medical imaging element support unit as claimed in claim 9, wherein the opening is a bore extending through the support body from one exterior surface to the skin engaging area.

11. The medical imaging element support unit as claimed in claim 9, wherein a cavity is annular and open across an area of said skin engaging area, the cavity forming an annular groove in the skin engaging area.

12. The medical imaging element support unit as claimed in claim 1, wherein the support body includes a cavity, the cavity comprising an opening across an area to be engaged with said skin engaging area, and the cavity having an air outlet fluidly connected with the air pump mechanism to permit evacuation of air from the cavity, to thereby create said suction force in response to the opening of the cavity being placed at the skin engaging area.

13. The medical imaging element support unit as claimed in claim 12, wherein the cavity is fluidly isolated from an opening for receiving at least a portion of the medical imaging element.

14. An ultrasound system, comprising a medical imaging element support unit as in claim 1, and the medical imaging element in the form of an ultrasound transducer unit received in the medical imaging element support unit.

* * * * *